(12) United States Patent
Burgstaller et al.

(10) Patent No.: US 9,910,024 B2
(45) Date of Patent: Mar. 6, 2018

(54) METHOD, SENSOR UNIT AND MACHINE FOR DETECTING "SUGAR TOP" DEFECTS IN POTATOES

(75) Inventors: Markus Burgstaller, Graz (AT); Peter Kerschhaggl, Raaba (AT); Marcus Groinig, Weissenstein (AT)

(73) Assignee: INSORT GMBH, Kirchberg an der Raab (AT)

( * ) Notice: Subject to any disclaimer, the term of this patent is extended or adjusted under 35 U.S.C. 154(b) by 678 days.

(21) Appl. No.: 13/812,439

(22) PCT Filed: Jul. 8, 2011

(86) PCT No.: PCT/EP2011/061607
§ 371 (c)(1),
(2), (4) Date: Jun. 5, 2013

(87) PCT Pub. No.: WO2012/013476
PCT Pub. Date: Feb. 2, 2012

(65) Prior Publication Data
US 2014/0056482 A1 Feb. 27, 2014

(30) Foreign Application Priority Data
Jul. 27, 2010 (AT) .............................. GM 473/2010

(51) Int. Cl.
*G01N 33/02* (2006.01)
*B07C 5/342* (2006.01)
(Continued)

(52) U.S. Cl.
CPC ......... *G01N 33/025* (2013.01); *B07C 5/3422* (2013.01); *G01N 21/85* (2013.01); *G01N 21/88* (2013.01)

(58) Field of Classification Search
CPC combination set(s) only.
See application file for complete search history.

(56) References Cited

U.S. PATENT DOCUMENTS 2,268,803 A * 1/1942 Cowl ................... B65G 17/063
                                                  198/384
3,664,397 A 5/1972 Raye et al.
(Continued)

FOREIGN PATENT DOCUMENTS

AT          12076 U1 * 10/2011 ........... B07C 5/3422
EP     0 058 028 A2     8/1982
(Continued)

OTHER PUBLICATIONS

Gowen et al., Hyperspectral imaging—an emerging process analytical tool for food quality and safety control. Trends in Food Science & Technology. 2007;18(2007):590-598.
(Continued)

*Primary Examiner* — Tsung-Yin Tsai
(74) *Attorney, Agent, or Firm* — Nutter McClennen & Fish LLP; John J. Penny, Jr.

(57) ABSTRACT

The invention relates to a method, a sensor unit and a machine for detecting "sugar end" defects in potatoes. The method comprises irradiating potatoes with at least one light source, for a plurality of locus points on each potato, wherein locus points lie on the end regions of the potato and other locus points lie in a central region of the potato. The light reflected from and/or transmitted through the respective locus points is selectively projected onto at least one photo sensor which generates light measurement signals for each locus point from the received light. At least one classification feature is determined from the light measurement signals. If at least one classification feature corresponds to a predefined "sugar end" criterion the respective potato is classified as having "sugar end" defects.

13 Claims, 5 Drawing Sheets

(51) Int. Cl.
*G01N 21/85* (2006.01)
*G01N 21/88* (2006.01)

(56) References Cited

U.S. PATENT DOCUMENTS

| | | | |
|---|---|---|---|
| 4,134,498 A | 1/1979 | Jones et al. | |
| 4,147,619 A | 4/1979 | Wassmer et al. | |
| 4,186,636 A | 2/1980 | Roberts | |
| 4,186,836 A * | 2/1980 | Wassmer | B07C 5/3422 209/565 |
| 4,262,806 A * | 4/1981 | Drabs | G01N 21/85 209/577 |
| 4,351,437 A | 9/1982 | Long | |
| 4,493,420 A * | 1/1985 | Dennis | B07C 5/3422 209/587 |
| 4,581,632 A | 4/1986 | Davis et al. | |
| 5,000,569 A * | 3/1991 | Nylund | G01N 21/8806 250/226 |
| 5,318,173 A * | 6/1994 | Datari | B07C 5/10 209/580 |
| 5,440,127 A * | 8/1995 | Squyres | B07C 5/3422 250/341.8 |
| 5,464,981 A * | 11/1995 | Squyres | B07C 5/3422 209/577 |
| 5,791,497 A * | 8/1998 | Campbell | B07C 5/3422 209/577 |
| 5,818,953 A * | 10/1998 | Queisser | G01N 21/88 209/580 |
| 5,884,775 A * | 3/1999 | Campbell | B07C 5/3422 209/581 |
| 6,512,577 B1 | 1/2003 | Ozanich | |
| 7,103,207 B2 | 9/2006 | Brown et al. | |
| 8,284,248 B2 * | 10/2012 | Bourg, Jr. | G01N 21/8851 348/89 |
| 2002/0011567 A1 * | 1/2002 | Ozanich | G01J 3/02 250/326 |
| 2005/0226465 A1 * | 10/2005 | Fujita | G06T 7/0004 382/110 |
| 2005/0254709 A1 | 11/2005 | Geshwind et al. | |
| 2012/0303157 A1 * | 11/2012 | Chung | B07C 5/3422 700/223 |

FOREIGN PATENT DOCUMENTS

| | | | |
|---|---|---|---|
| EP | 0 375 881 A1 | 7/1990 | |
| EP | 0 672 468 B1 | 9/1999 | |
| EP | 0 939 316 A2 | 9/1999 | |
| EP | 1 679 496 A1 | 7/2006 | |
| EP | 1 332 353 B1 | 12/2009 | |
| GB | 2 466 621 A | 6/2010 | |
| JP | 2000111473 A * | 4/2000 | |
| JP | 2006170718 A * | 6/2006 | G01N 21/3581 |
| WO | 99/61898 A1 | 12/1999 | |
| WO | 2010/025254 A1 | 3/2010 | |

OTHER PUBLICATIONS

International Search Report mailed Sep. 30, 2011 for Application No. PCT/EP2011/061607 (14 Pages).

International Preliminary Report on Patentability mailed Feb. 7, 2013 for Application No. PCT/EP2011/061607 (10 Pages).

* cited by examiner

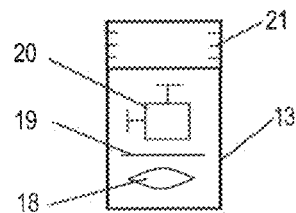
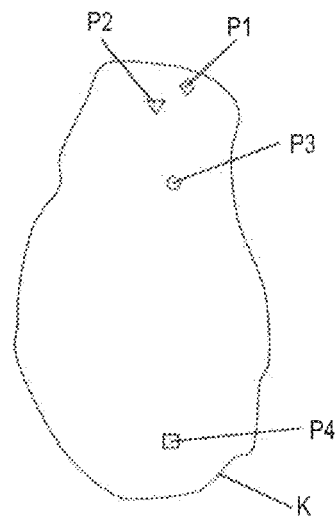
Fig. 3
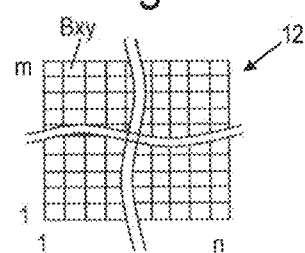
Fig. 4
Fig. 5
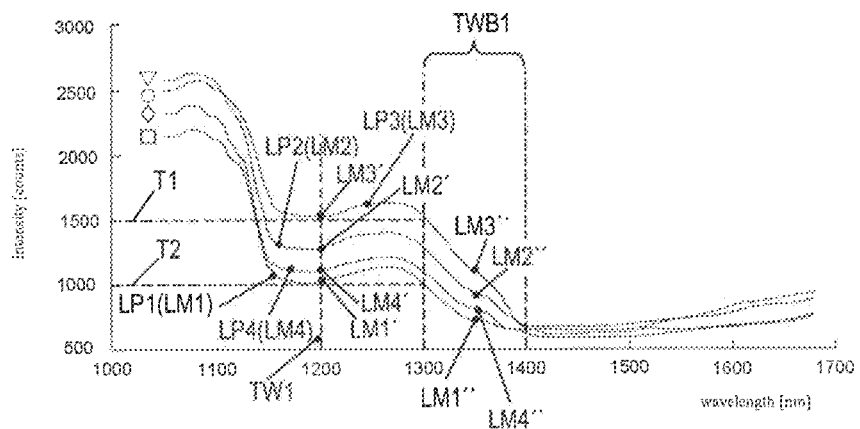
Fig. 6

METHOD, SENSOR UNIT AND MACHINE FOR DETECTING "SUGAR TOP" DEFECTS IN POTATOES

BACKGROUND OF THE INVENTION

The invention relates to a method and a sensor unit for detecting "sugar end" defects in potatoes.

The invention further relates to a machine for treating potatoes having "sugar end" defects.

The detection and subsequent sorting of bulk material using cameras is a rather common method. One embodiment of such a plant for sorting potatoes is, e.g., described in the patent U.S. Pat. No. 4,351,437A. In this known plant, potatoes are conveyed on a roller table conveyor, wherein they are moved arranged in transverse rows to an inspection region, in which they are irradiated by light in an incident light method and the light reflected from the potatoes is captured by a line scan camera. The line scan camera regularly scans transversely across each row of potatoes and generates a detection output signal corresponding to the reflected light. The camera thus views a brightly illuminated region of the potatoes against a dark background so that a microprocessor may determine from the images captured in this way the length of the potatoes in the direction of the row of potatoes.

Further plants for sorting and analyzing foodstuff are described in EP 672 468 B1 or EP 1 332 353 B1. Most common is the incident light detection and sorting of conveyed objects, wherein the conveyed objects are inspected completely automatically, wherein light is projected onto the objects and the reflected light is received by a camera and then analysed. The light is either wide-band or filtered white light, it may also be configured as LED or laser light having particular wavelengths for the relevant task to be performed. Impurities at the object surface may be recognized using this technology, but also certain quality differences in the bulk material.

Recently, more and more spectroscopic technologies have been used for analyzing and inline sorting foodstuff. By means of a so-called "flavour" or "taste analyser", the sugar content of entire fruits is being analysed, for example. An embodiment of such a device is described in the patent U.S. Pat. No. 7,103,207 or configured as a hand-held tool in WO 99/61898 A1. These methods function on the basis of a single-channel spectrometer. Therewith, the reflectance and/or transmission behaviour of a single measurement point or measurement spot of an object is recorded and analysed.

Many defects and impurities of fruits and vegetables, however, cannot be recognized using these known technologies. In particular the so-called "sugar end" defects and potatoes, which are known in the literature as "sugar-ends", cannot be clearly recognised, as these are local defects of growth in the potato tuber. In these local growth defects, there is developed an accumulation of sugars at the stem end, in particular at the proximal end of the potato tubers, caused by various environmental factors. Especially potatoes of long tubers are prone to these "sugar end" defects, such as, for example, the sorts "Russet Burbank" and "Shepody" that are frequently used for the production of French fries. This growth defect is of great economic importance, as the locally accumulated reducing sugars generate brown to black pigments in the course of heating, thus making the final potato product optically non-appealing and, hence, non-marketable. An essential problem of the "sugar end" defects is that they are not optically recognizable at the raw potatoes or potato parts, respectively, but will rather appear following heating in the kitchen or in the food processing industry, respectively, and will then result in frequent complaints. An additional aspect of at least one embodiment of the invention is the prevention of increased acryl amide formation when the potatoes are baked or fried. In particular French fries have become ill-famed as they contain acryl amide, a substance that may cause cancer. Acryl amide is generated when potatoes are baked or fried at high temperatures, by the starch contained in the potatoes being overheated. The most important starting material for acryl amide in foodstuff is the amino acid asparagine, predominantly present in potatoes and corn. The formation of acryl amide is further promoted by sugars such as glucose, this is substances which are also present in larger quantities in potatoes having "sugar end" defects.

Former approaches to the early recognition of "sugar end" defects on potatoes are based on heating test samples of potatoes upon harvest or at incoming goods inspections, followed by visual inspection by the operator personnel. If individual test samples show "sugar end" defects, rather frequently the entire charge of the potatoes is discarded, amounting for huge material losses and large losses for the producing company. Alternatively, all ends of the potatoes of the entire charge are cut off, if "sugar end" defects are present on the test sample. In this way, the material loss is decreased, due to the additional working process step of cutting off, however, the costs of labour and machines are increased. Furthermore, heating and inspecting test samples constitutes a time-consuming task, hindering a rapid processing of the potatoes.

Hence, it would be desirable to provide a method and a sensor unit for detecting "sugar end" defects in potatoes, which are not simply applied to test samples but rather enable a reliable examination of all potatoes, and this, moreover, inline in a single potato processing line. It would be further desirable to provide a machine for treating potatoes having "sugar end" defects, in which initially potatoes having "sugar end" defects are reliably detected and subsequently the potatoes having "sugar end" defects are either sorted out or treated by cutting off the parts in question.

SUMMARY

At least one embodiment of the present invention solves the above task by providing a method for detecting "sugar end" defects on potatoes with the characterising features of claim 1. Advantageous configurations of the invention are presented in the following description and the sub-claims.

The method according to at least one embodiment of the invention for detecting potatoes having "sugar end" defects comprises:

irradiating potatoes with at least one light source, for a plurality of locus points on each potato, wherein locus points lie on both end regions of the potato and other locus points lie in a central region of the potato, selectively projecting the light reflected from and/or transmitted through the respective locus points onto at least one photo sensor, generating, by means of the at least one photo sensor, light measurement signals for each locus point from the received light and intermediately storing such light measurement signals generated for each locus point, determining at least one classification feature from the light measurement signals and classifying potatoes as having "sugar end" defects if at least one classification feature corresponds to a predefined "sugar end" criterion.

In principle, it would be sufficient to recognize locus points on each end region of the potato, in which the weed is growing, and in a central region. In practice, however, in the processing of potatoes, the weed has already been removed from the potato tuber when the "sugar ends" are detected and the potato may have rotated several times in the course of transport, so that that for a practicable embodiment of the invention there is provided that locus points on both end regions of the potato and other locus points in a central region of the potato are captured.

With the inventive method, "sugar end" defects may be detected in unmoved, intermittently moved and in continuously moved potatoes.

The term "potato" as used herein comprises entire potatoes as well as potato pieces, in particular strip-like or disc-like potato pieces that are cut in the longitudinal or in the transverse direction.

If the light reflected from and/or transmitted through the locus points is sequentially projected onto the at least one photo sensor, a single photo sensor is sufficient because of this spatial multiplex method. Therein, locus points are scanned one after the other. The light reflected from and/or transmitted through the locus points may then be, for example, projected onto the photo sensor using a two-dimensionally movable mirror.

If the potatoes are moved along a conveying direction at a defined conveying velocity and if the light reflected from or transmitted through the locus points is projected onto the same photo sensor spaced apart in time, a time multiplex method is taking place in the conveying direction. In order to make it possible to scan the reflected or transmitted light of randomly distributed locus points by way of one photo sensor, local scanning transversely or obliquely to the conveying direction, for example following a line, will suffice. If a plurality of photo sensors are arranged transversely to the conveying direction instead of only one single photo sensor, deflection means for the light reflected from or transmitted through the locus points are not necessary. Viewed in the conveying direction, locus points that are situated one after the other are rather associated with the same photo sensor and scanned in the time multiplex method when the potatoes are being moved.

According to a first approach for determining at least one classification feature from the light measurement signals and classifying potatoes as having "sugar end" defects, if at least one classification feature corresponds to a predefined "sugar end" criterion, there is provided to make provision of at least one photo sensor, which is sensitive only to one single wavelength or a wavelength band within the frequency band of the narrow-band or filtered, respectively, light source. There may also be provided several photo sensors, which are sensitive to various wavelengths or wavelength bands. The light measurement signals of the at least one photo sensor are representative light intensity values for the single wavelength or wavelength band, or for several wavelengths or wavelength bands spaced apart, wherein the classification feature is these light intensity values and the "sugar end" criterion is defined as the deviation from a threshold light intensity value. The light intensity values at the particular wavelengths or wavelength bands may be obtained as follows:

parallel or sequential irradiation of the potatoes with narrow-band light at the particular wavelengths or wavelength bands; and/or irradiation of the potatoes with wide-band light and filtering of the light reflected and/or transmitted at the respective locus points with band pass filters, the band pass of which contain the particular wavelengths or wavelength bands; and/or provision of photo sensors, which are sensitive in the particular wavelengths or wavelength bands.

In a more general approach of at least one embodiment of the invention, by means of which an improved classification result for "sugar end" defects in potatoes may be obtained, the irradiation of the potatoes is realized using a wide-band light source. By means of the at least one photo sensor, for all locus points the spectra of the light reflected from and/or transmitted through the locus points are generated as light measurement signals. This requires that for the provision of a single photo sensor this photo sensor has to be adapted to split up the spectrum. Alternatively, there may be provided several photo sensors, which are sensitive to different partial frequency ranges of the spectrum. From the determined spectra or the nth (n=1, 2, ... ) derivative of the spectra there will be determined at least one classification feature.

In an embodiment of the invention that is preferred because of its preciseness, the respective light reflected from and/or transmitted through the locus points is captured by splitting up the spectrum in a plurality of spectral components, and each spectral component is then projected onto a light-sensitive pixel that is associated with this spectral component of a photo sensor equipped with a plurality of pixels. The pixels may be arranged in one line (line sensor), wherein the light reflected from or transmitted through the respective locus point is sequentially (in the multiplex method) spectrally split up for each locus point and projected onto all pixels of the line sensor. The spectral light measurement signals that are such sequentially generated for each locus point are intermediately stored as a two-dimensional image, the first dimension of which representing the locus points and the second dimension of which representing the spectral components of the radiation. As an alternative to the line sensor, the pixels of the photo sensor are arranged in a two-dimensional way (area sensor), wherein the first dimension represents the locus points and the second dimension represents the spectral components of the light.

By splitting up and intermediately storing the light reflected from or transmitted through the respective locus points into the spectral components thereof, it is possible to determine the at least one classification feature from the respective spectrum or the nth derivative of the respective spectrum of the locus points. This determination of a classification feature comprises calculating a difference curve for the respective locus point by calculating the differences between the spectral light measurement signals of the respective locus point and the spectral values of a reference spectrum for a number of wavelengths or by calculating the differences between the nth derivative of the spectral light measurement signals of the respective locus point and the nth derivative of the reference spectrum for a number of wavelengths, wherein the classification features is thus determined by the difference curve calculated in this way.

In another embodiment of the invention, in which the classification feature is determined from the difference curve calculated as described in the previous paragraph, a classification feature derived from the difference curves is the intensity curve of the respective difference curve over the wavelength. In this case, the classification criterion is selected from exceeding or falling below the intensity limit values at the defined wavelengths or wavelength bands, optionally with calculating average values of the intensity values within the wavelength bands. As an alternative or additional classification criterion, the presence of intensity values within or out of a defined intensity value range at defined wavelengths or wavelength bands may be defined, optionally with calculating average values of the intensity values within the wavelength bands. As a further alternative or additional classification criterion may be defined the similarity of at least one portion of the intensity curve with a predefined pattern.

In a further embodiment of the invention, wherein the classification feature is determined from the difference curve calculated as described above, a classification feature derived from the difference curves is the curve of the first or second differential quotient of the respective difference curve. In this case, the classification criterion is selected from exceeding or falling below the limit values of the differential quotient at defined wavelengths or wavelength bands, optionally with calculating average values of the differential quotient values within the wavelength bands. As an alternative or additional classification criterion may be defined the presence of differential quotient values within or out of a defined differential quotient value range at defined wavelengths or wavelength bands, optionally with calculating average values of the differential quotient values within the wavelength bands. As another alternative or additional classification criterion may be defined the similarity of at least one portion of the differential quotient curve with a predefined pattern. It is to be noted that in the practical computer-based realisation of the invention the differential quotient itself is usually not calculated but there is rather performed an approximate calculation of the differences quotient. This, however, is equivalent to the differential quotient calculation for the purpose of the present invention.

In a preferred embodiment of the invention a classification feature derived from the difference curve is obtained from the at least portion-wise transformation of the difference curves into a visible wavelength range, by means of which false-colour images are obtained. Preferably, there are transformed at least three portions of the difference curves into visible wavelength ranges. The classification criterion is in this embodiment the locally defined appearance and/or absence of colours or colour ranges or colour transitions in the false-colour images, wherein not only specific colours but rather also colour ranges that are designated as "colour clouds", similar colours, etc. are used. This embodiment shows several advantages. It allows for the visual inspection by the operating personnel, e.g., as a monitoring means or in the initial implementation of a plant for detecting potatoes having "sugar ends". This embodiment further allows for the further processing of the transformed wavelength ranges using well-established image processing means, thus essentially simplifying implementation by way of software, as, in part, there may be referred back to standard routines. Finally, the at least portion-wise transformation of the difference curves into a visible wavelength range may also compensate heterogeneities of the potatoes to be examined, which is advantageous in particular for the visual inspection by the operating personnel.

In a further especially advantageous embodiment of the invention, the reference spectrum is calculated as an averaged spectrum from the spectral image data of locus points of at least one potato, preferably from the spectral image data of locus points, which are associated with a central area of one or several potatoes. In this way, there is generated a very reliable reference spectrum, without complex calibration or adjustment works being required or special know-how of the operating staff being necessary. This will greatly simplify the installation and operation of plants in the industrial field, in which the present invention is implemented.

In a development of the above described method for calculating a reference spectrum there is provided that the reference spectrum is calculated or updated as a locally or timely averaged spectrum from the spectral image data of locus points of one or several of the potatoes to be examined in regard to "sugar end" defects, optionally while the potatoes are moved along the conveying direction. This embodiment allows for the determination of a reference spectrum directly from the potato bulk to be examined, wherein this reference spectrum may be updated continuously or at certain time intervals or, e.g., manually in the course of a quality assurance inspection.

In another embodiment of the invention determining at least one classification feature from the respective spectrum or the nth derivative of the respective spectrum of the locus points comprises calculating the concentrations of ingredients such as e.g., glucose, starch, solids, and or capturing the glassiness from the spectrum of the nth derivative of the spectrum of the respective locus point. The classification features are selected from the determined concentration values of the ingredients or combinations thereof, such as, e.g., the ratio of glucose to starch and/or the glassiness. In this embodiment, hence, the detection of "sugar end" defects is carried out by analysing particular ingredients or the glassiness (an optical feature) from the spectra or the derivatives thereof and by subsequently drawing conclusions from the ingredients or the glassiness, respectively, to the possible presence of "sugar end" defects.

In a development of the method described in the above paragraph, from the spectrum or the nth derivative of the spectrum of at least one locus point there are determined reference concentrations of ingredients such as, e.g., glucose, starch, solids, and/or the glassiness, wherein the locus point lies preferably in a central region of a potato. Optionally there is used a plurality of locus points wherein the average value of their spectra or the nth derivative of the spectra is calculated. The deviation of the determined reference concentration values of the ingredients or combinations thereof such as, e.g., the ratio of glucose to starch, and/or the reference glassiness, of concentration of ingredients or combinations thereof and/or of the glassiness at locus points, which lie on the end regions of potatoes, represent a "sugar end" criterion in this embodiment of the invention. Due to this automatable determination of reference concentrations of ingredients and/or a reference glassiness, complex calibration or adjustment works for obtaining these reference values are prevented. Also special know-how of the operating personnel is not required. Another huge advantage is that the determination of the mentioned reference values may be realised online, without interruption of the operation of the plants, in which the present invention is implemented.

At least one embodiment of the present invention solves the initially posed task by providing a sensor unit for detecting "sugar end" defects in potatoes, comprising:
  at least one light source for irradiating the potato,
  at least one photo sensor,
  an optics, by means of which the light reflected and/or transmitted at the locus points on each potato is selectively projected onto the at least one photo sensor,
  wherein the at least one photo sensor generates from the received light for each locus point light measurement signals,
  an intermediate storage, by which the light measurement signals generated by the at least one photo sensor are stored for each locus point,
  characterized by
  calculation means, which carry out the method for detecting "sugar end" defects in potatoes according to the claims, wherein the calculation means classify the potatoes as having "sugar end" defects and emit a "sugar end" signal, if at least one classification feature corresponds to a predefined "sugar end" criterion.

It has been shown that the detection of "sugar end" defects on potatoes provides especially reliable results if the at least one light source emits light in a wavelength range between at least 350 and 2500 nm. Within this wavelength range, the partial wavelength ranges of 1000-1700 nm (so-called NIR range) and/or 350-1000 nm (so-called VISNIR range) and/or up to 2500 nm (so-called SWIR range) are preferred. These mentioned partial wavelength ranges may be determined by the following types of photo sensors: silicon sensors for wavelengths from 350 to 1000 nm, indium-gallium-arsenide sensors for wavelengths from 900 to 1700 nm, mercury-cadmium-telluride (MCT) sensors for wavelengths from 800 to 2500 nm For the continuous detection of "sugar end" defects in potatoes there is provided that the sensor unit be equipped with conveyor means, on which the potatoes are moved along a conveying direction at a defined conveying velocity. For the determination of the light reflected from or transmitted through the different locus points, the conveyance of the potatoes is a time-multiplexing method. This means that there has to be performed a local determination of the light reflected from or transmitted through the various locus points only transversally to the conveying direction, whereas locus points that are situated one after the other in the conveying direction are processed by the time multiplexing determined by the conveying velocity.

In order to reduce the number of photo sensors (in the extreme case to only one single photo sensor), in one embodiment of the invention the optics comprises movable light deflection means, by means of which light reflected from and/or transmitted through the locus points is sequentially projected onto the at least one photo sensor. In an alternative embodiment, by means of which a faster detection of "sugar end" defects on potatoes is possible, there is, however, provided a plurality of photo sensors.

In order to guarantee that the light reflected from or transmitted through the locus points and received by the at least one photo sensor is within a wavelength range suitable for the photo sensor, because of which the quality of measurement is improved, there is provided in a development of the invention that the optics comprises band pass filters or a spectrograph.

In order to enable a faster online inspection of potatoes in regard to the presence of "sugar end" defects, and in order to obtain a more compact setup of the sensor unit, it is useful to use photo sensors having a plurality of light-sensitive pixels, wherein optionally the pixels of the photo sensor are arranged in a two-dimensional way, with the first dimension representing the locus points and the second dimension representing the spectral components of the light.

At least one embodiment of the present invention further comprises a machine for treating potatoes having "sugar end" defects. This machine comprises a conveyor device for continuously conveying potatoes along a conveying direction at a defined conveying velocity, a treatment device for potatoes and a sensor unit according to the invention as described above, wherein a "sugar end" signal emitted by the sensor unit controls the treatment device. The treatment device comprises in a first embodiment potato sorting means, which, in the case of a "sugar end" signal, sorts out the potato associated with this signal. In a further embodiment of the invention, the treatment device comprises a cutting device for cutting off the ends of entire potatoes or longitudinally cut potato pieces having "sugar end" defects.

BRIEF DESCRIPTION OF THE DRAWINGS

The invention is now described in detail by way of exemplary embodiments in reference to the drawings.

FIG. 3 shows a schematic illustration of an optics used in a sensor unit according to at least one embodiment of the invention.

FIG. 4 shows a schematic top view of a photo sensor that is sensitive to a plurality of different wavelengths and locally defined pixels.

FIG. 5 shows a schematic depiction of a potato having exemplary locus points.

FIG. 6 shows a diagram of the light intensity over the wavelength of spectral light measurement signals at locus points of a potato.

DESCRIPTION OF THE PREFERRED EMBODIMENTS

Figure 1:
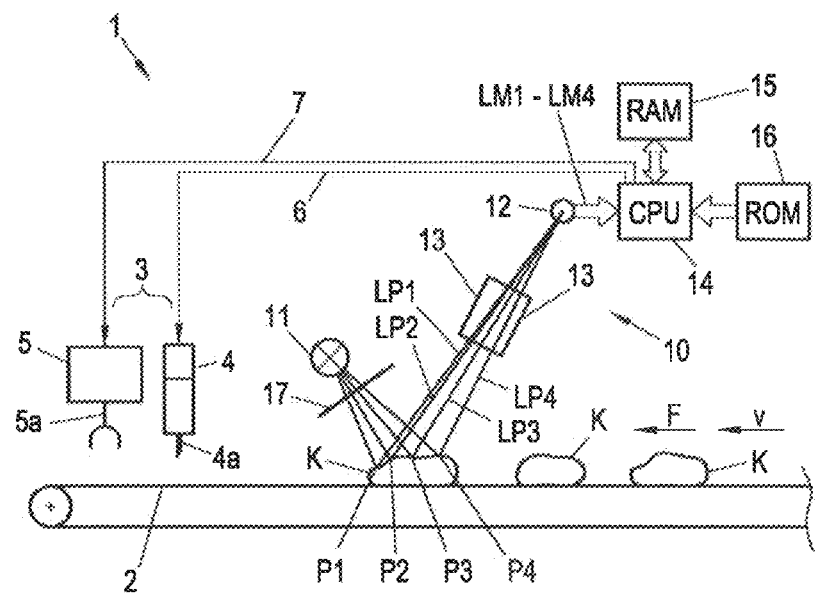
FIG. 1 schematically shows in a lateral view a machine for treating potatoes having "sugar end" defects.
Figure 2:
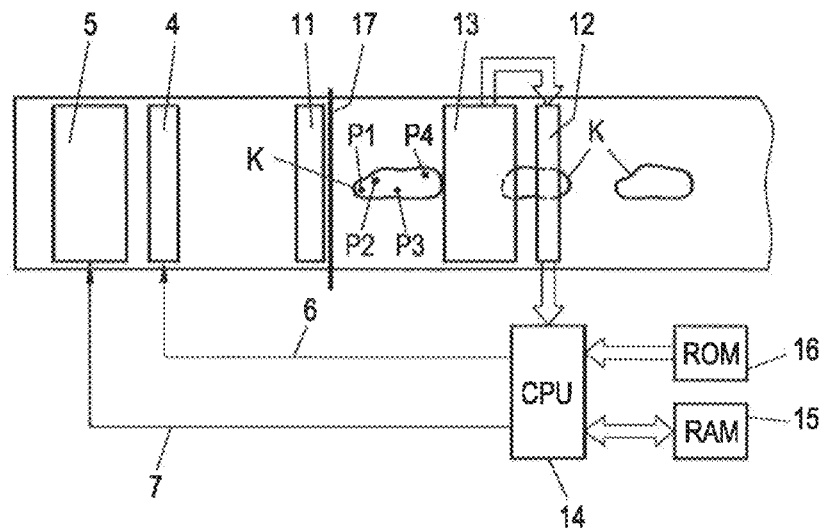
FIG. 2 shows the machine according to FIG. 1 schematically in a top view.

In the FIGS. 1 and 2 there is schematically depicted in a lateral view and a top view, respectively, an inventive machine 1 for detecting and treating potatoes K having "sugar end" defects. The machine 1 comprises a conveyor device 2 for continuously or discontinuously conveying potatoes K along a conveying direction F. In the case of continuous conveyance, this is carried out at a defined conveying velocity v. The conveyor device 2 may be configured, for example, as a conveyor belt, roll conveyor, chute or anything similar. The machine 1 further comprises a treatment device 3 for potatoes K. This treatment device 3 comprises potato sorting means 5 and/or a cutting device 4 for cutting off the ends of potatoes having "sugar ends". In the FIGS. 1 and 2 there are schematically illustrated the potato sorting means 5 having a gripper 5a. It is to be understood, however, that instead of the gripper there may also be used other means such as ejector means (e.g., on the basis of air or spring) or deflection means or trap doors, etc. The cutting device 4 is illustrated having a guillotine-like knife 4a; there are, however, also possible other knives known to those skilled in the art.

The core element of the machine 1 is a sensor unit for detecting "sugar end" defects on potatoes, which is generally designated with the reference number 10 and is subsequently described in greater detail. When the sensor unit 10 detects a potato K having "sugar end" defects, it generates a "sugar end" signal 6, 7, which is transmitted to the treatment device 3 and triggers an according treatment of the potato K. This treatment will either comprise sorting out the potato K by the potato sorting means 5 or cutting off the parts of the potato K having "sugar end" defects. It is to be noted that the term "potato K", as used herein, covers entire potato tubers as well as potato pieces, in particular strip-like or disc-like potato pieces cut in the longitudinal or transversal direction. As "sugar end" defects appear only at the end regions of potato tubers, sorting by means of potato sorting means 5 is useful only for transversely cut potato pieces.

The sensor unit 10 for detecting "sugar end" defects on potatoes comprises one or several light sources 11 for irradiating the potatoes K, at least one photo sensor 12, an optics 13, by means of which light LP1-LP4 reflected and/or transmitted at the locus points P1-P4 at each potato K is selectively projected onto the at least one photo sensor 12. The at least one photo sensor 12 generates from the received light LP1-LP4 for each locus point P1-P4 light measurement signals LM1-LM4 and transmits those by means of computing means 14 to an intermediate storage 15, in which the light measurement signals LM1-LM4 are stored for each locus point P1-P4. The computing means 14 are controlled by a programme code stored in a programme memory 16 in order to process a method for detecting "sugar end" defects in potatoes. In the method that is subsequently explained in greater detail, from the light measurement signals LM1-LM4, optionally with previously performing a pre-processing in order to process the light measurement signals LM1-LM4 into a form that is faster to be processed and/or has a lower error rate, the potatoes are classified as having "sugar end" defects, if at least one classification feature corresponds to a predetermined "sugar end" criterion; in this case, a "sugar end" signal 6, 7 is transmitted to the treatment device 3.

It has been shown that potatoes K having "sugar end" defects may be detected in a very reliable way if light measurement signals LM1-LM4 within a wavelength range between 350 and 2500 nm are evaluated, wherein within this wavelength range there may be evaluated one or several specific wavelengths or wavelength bands. In order to reduce the computing effort and to minimize the influence of interfering light, it is useful to keep the irradiation by the at least one light source 11 within the mentioned wavelength range and also to tune the sensitivity of the photo sensors 12 thereto. This may be achieved by using one or several narrow-band light sources 11 (light diodes, laser etc.) or if a wide-band light source 11 having a preliminary filter 17 is used, which only allows light in the wavelength range between 350 and 2500 nm or in partial wavelength ranges thereof, respectively, to pass through. As photo sensors 12 there may be used several photo sensors, which each are sensitive to different partial wavelength ranges. Such partial wavelength ranges are, for example, the partial wavelength ranges from 900-1700 nm (NIR) and/or 350-1000 mm (VISNIR) and/or up to 2500 nm (SWIR). Photo sensors 12, which are suitable for these partial wavelength regions, are, for example, silicon sensors having a main sensitivity of 350-1000 nm, indium-gallium-arsenide sensors having a main sensitivity of 900-1700 nm, and mercury-cadmium-telluride (MCT) sensors having a main sensitivity of 800-2500 nm.

It is to be noted that in the illustrated exemplary embodiment the light source 11 and the photo sensor 12 are arranged at the same side of the potato K, so that the light LP1-LP4 reflected from the locus points P1-P4 reaches the photo sensor 12. If the light source 11 is placed underneath the conveyor device 2, the light transmitted from the locus points P1-P4 reaches the photo sensor 12. In the latter arrangement the conveyor device 2 is to be either configured with translucent elements, or there are to be provided elements, e.g., conveyor belt elements or rollers, spaced apart from each other in order to make it possible for the light to pass through, or if a chute is used, there may be implemented a gap, or it may be measured at the end of the conveying section "in free fall".

It is the task of the optics 13 to guide the light LP1-LP4 reflected from or transmitted through the locus points P1-P4 in a suitable way to the at least one photo sensor 12. As schematically depicted in FIG. 3, the optics 13 further comprises for this purpose in general at least on optical lens 18 as well as optionally at least one band pass filter 19 and/or light deflection means 20, for example, a mirror that may be deflected along one or two axes. If the light deflection means 20 may be deflected only along one axis, the optics 13 is then adjusted such that light scanning is performed transversely to the conveying direction F (so-called spatial multiplexing). Taking into account also the movement of the potatoes K in the conveying direction F at the conveying velocity v (so-called time multiplexing), there may be realised a sequential two-dimensional scanning, wherein one single photo sensor 12 is sufficient (combined time and spatial multiplexing). For a higher processing velocity, the provision of several photo sensors 12, which work in parallel, is useful, wherein the photo sensors are sensitive to different wavelength ranges and/or cover different locus points P1-P4. If a plurality of photo sensors 12 is arranged distributed transversely to the conveying direction F (line sensor), locus points that are—viewed in the conveying direction F—situated one after the other are associated respectively to one and the same photo sensor. For an increased wavelength resolution, the optics 13 may also comprise a spectrograph 21.

In FIG. 4 there is schematically depicted in top view a preferred two-dimensional photo sensor 12, which has in a rectangular arrangement a plurality of light-sensitive pixels Bxy. The lines 1-m represent locally defined locus points, the columns 1-n represent the various spectral components of the light reaching the photo sensor. In a simplified version of this photo sensor, which is to be combined with a spatial multiplexing by way of light deflection means 20, the number n of the present or used columns is chosen to be 1.

FIG. 5 shows four exemplary locus points P1-P4 on a potato K. The locus points P1 and P2 are present at the proximal end of the potato, from which weed is growing (not depicted). P3 is a locus point near the centre, and P4 is a locus point at the distal end of the potato K. In the irradiation by light from the light source 11, the light LP1-LP4 reflected from the locus points P1-P4 is depicted in the wavelength/intensity diagram of FIG. 6 in spectral resolution in a wave length range of 1000 to 1700 nm.

If the two-dimensional photo sensor 12 shown in FIG. 4, which allows for splitting of the received light for each locus point, is used for capturing the light LP1-LP, the intensities of the light LP1-LP4 reflected from the locus points P1-P4 essentially correspond to the light measurement signals LM1-LM4 generated by the photo sensor for each locus point P1-P4, which are stored in the intermediate storage 15 for further processing.

If there is used, however, a photo sensor 12, which is only sensitive to the partial wavelength TW1 (e.g., at 1200 nm), such a photo sensor 12 will provide for the light LP1-LP4 received from each locus point P1-P4 only one respective intensity value as light measurement signal LM1'-LM4'.

If the photo sensor 12 is used, which is only sensitive to a partial wavelength band TWB1 (e.g., between 1300 and 1400 nm), such a photo sensor 12 will provide for the light LP1-LP4 received from each locus point P1-P4 only one respective averaged intensity value as light measurement signal LM1"-LM4".

As one can clearly see in the diagram of FIG. 6, the signal forms of the light LP1-LP4 reflected from the locus points P1-P4 are similar to each other, deviating, however, in their signal amplitude and partially overlapping each other. Anticipating the subsequent explanation, it is to be noted that this potato is a potato having a "sugar end" defect. The detection of this defect is realised using the photo sensor 12 that is only sensitive to the partial wavelength TW1 of 1200 nm by way of comparison of the light measurement signals LM1'-LM4' represented by the light intensity values, which in this case constitute the classification feature, with a first threshold light intensity value T1 of, e.g., 1500 relative light intensity units. Deviating from, more precisely, falling below the light intensity values of this threshold light intensity value T1 is defined as the "sugar end" criterion. As one can see in the diagram of FIG. 6, except for the light measurement signal LM3' all other light measurement signals LM1', LM2', LM4' fall below the threshold light intensity value T1, this showing that the potato K does have a "sugar end" defect. Actually, however, only the regions of the potato around the locus point P1 (surely) have a "sugar end" defect, and those around the locus point P2 (possibly) have a "sugar end" defect, whereas the detection of a "sugar end" defect at the locus point P4 is a wrong interpretation, which may occur in a disadvantageous light situation or due to mere consideration of absolute light intensity values. Using the photo sensor 12 that is sensitive for the partial wavelength band TWB1 between 1300 and 1400 nm will provide the same result. Also herein, in comparison with a second threshold light intensity value T2 of, e.g., 1000 relative light intensity units, the averaged intensity values of the light measurement signals LM1", LM2", LM4" of the locus points P1, P2, P4 are below the second threshold light intensity value T2, and only the light measurement signal LM3" or the averaged intensity value thereof of the locus point P3, respectively, is above the second threshold light intensity value T2. In order to increase measurement reliability, there might, for example, be made use of the brightness at 1050 nm as "reference brightness", to which the measurement results may be referred to. Thereby, illumination effects may be eliminated.

Also anticipating the subsequent explanation, there is to be noted herein that from the light LP1-LP4 or the light measurement signals LM1-LM4 generated by a spectrally resolving photo sensor 12, respectively, at the beginning of the processing or also in operation, there may be obtained reference spectra, e.g. by using the light measurement signal LM3 of the centre-near locus point P3 as reference spectrum, or by determining from the light measurement signals LM1-LM4 of several or all locus points P1-P4 through average value calculation a reference spectrum, or according to another method described further below.

As one can see from the diagram of FIG. 6, the light intensity values of the light measurement signals LM1'-LM4' and LM1"-LM4", respectively, are situated rather closely together. In their use as classification feature and according to the "sugar end" criterion defined as deviation from a threshold light intensity value, this will sometimes result in an undesired high erroneous detection rate. This error rate may be clearly reduced if the irradiation of the potatoes is performed with wide-band light and if the spectra of the light LP1-LP4 reflected from and/or transmitted through the locus points P1-P4 are determined as light measurement signals LM1-LM4, such as it is possible with the photo sensor 12 illustrated in FIG. 4. From the signal curves, this is the spectra of the light measurement signals LM1-LM4, there may be established significant classification features and "sugar end" criteria on the basis of curve sketching, such as, e.g., inclines or curvatures at certain wavelengths. Another increase of the significance of the evaluable signals may be obtained by calculating the nth (n=1, 2, . . . ) derivative of the spectra, this is the light measurement signals LM1-LM4, and thereto applying means of curve sketching as classification features and "sugar end" criteria. By calculating the derivatives, the amount of the direction changes of the curvatures is increasing, thus generating information, from which the amount of the sugar may be better characterised.

Figure 7:
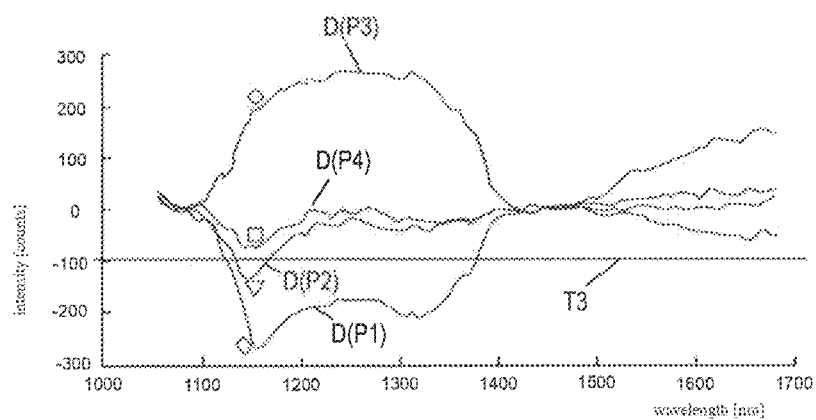
FIG. 7 shows a diagram of the light intensity over the wavelength of the difference curves of spectral light measurement signals at locus points of a potato to a reference spectrum.

It is to be noted that the spectral light measurement signals LM1-LM4 may be subjected to pre-processing before their processing. Pre-processing of spectra includes the following functions:
    intensity compensation
    defect pixel treatment
    noise suppression
    local correction
    derivative ($1^{st}$ and $2^{nd}$ derivative)
    standardisation
    smoothing In a further variant of the detection of "sugar end" defects on potatoes there is determined a classification feature from the respective spectrum or the nth derivative of the respective spectrum of the locus points P1-P4 by calculating, as depicted in the diagram of FIG. 7, a difference curve D(P1), D(P2), D(P3), D(P4) for the respective locus point P1-P4 by calculating the differences between the spectral light measurement signals of the respective locus point and the spectral values of a reference spectrum for a series of wavelengths or by calculating the differences between the nth derivative of the spectral light measurement signals of the respective locus point and the nth derivative of the reference spectrum for a series of wavelengths. The classification feature is determined on the basis of the thus calculated difference curves, for example, by defining a third threshold light intensity value T3 and by defining the "sugar end" criterion as falling below the threshold light intensity value T3 in a wavelength range, e.g., between 1150 and 1300 nm, or even at a single wavelength, e.g., at 1150 nm. As one can see from the diagram of FIG. 7, the difference curves D(P1), D(P2), D(P3), D(P4) for the respective locus point differ greatly, and without any doubt, the difference curve D(P1) of the locus point P1 indicates a "sugar end" defect, in contrast to the difference curve D(P3) of the locus point P3 situated near the centre.

The difference curves are in the following designated as difference spectrum. Analogously, this also includes the difference curves of the $1^{st}$ and $2^{nd}$ derivative.

Definition:

Minuend spectrum: currently measured spectrum (of a locus point)

Subtrahend spectrum: reference spectrum (stored in the storage)

To start with, the difference spectrum ($\Delta r$) for the subtrahend spectrum (r) is calculated:

$$\Delta r = \text{DiffSpectra}(x, r_{norm}, k, d)$$

with:
x=minuend spectrum (currently measured spectrum)
r_norm=the subtrahend spectrum standardised to 1 (reference spectrum)
k and d: determine standardisation $\Delta r$ shows large deviations if the minuend spectrum x is unlike r_norm and small ones if both are similar.

In the following, the inline calculation of a reference spectrum during the operation or the calculation of the nth derivative of the reference spectrum, respectively, is explained.

The subtrahend spectrum (reference spectrum) is subtracted from the minuend spectrum (current spectrum). The subtrahend spectrum may be adapted in the course of the detection of "sugar end" defects on potatoes.

Adjustment of the subtrahend spectrum for changing potato bulks is necessary. It has been shown that a sugar end that is quite well pronounced at harvest time and has a high sugar concentration locally compacted at the proximal end of the potato will start to spread towards the centre of the potato during storage. In this way, the sugar end will increase in size during storage exhibiting lower local sugar concentrations.

Method 1 for the Inline Determination of the Subtrahend Spectrum (Averaged Centre Spectrum)
  Inline determination of the locally central part of the potatoes (via object formation measures)
  Averaging of all spectra of all detected potatoes in this region. Only sustainable (no short-term) changes will be included in the subtrahend spectrum (I behaviour)

$$r = \frac{1}{1+G}(r + Gx_{potato})$$

with:
r=subtrahend spectrum
x_potatoe=spectrum of the currently viewed potato averaged (locally) over the central region
G=weight factor, this including newly detected centre spectra into the change of the subtrahend spectrum.

Method 2 for the Inline Determination of the Subtrahend Spectrum (Integrated Potato Spectrum)
  In comparison with method 1, this method has the advantage that determination of the central region is not necessary.
  Initially, there is given a subtrahend spectrum (=spectrum of a healthy potato). All minuend spectra, independent of the localisation on the potato, having only a slight deviation to the subtrahend spectrum, will be included in the running evaluation and optionally in an adjustment of the subtrahend spectrum. Slight deviations from the reference correspond to a healthy potato, large deviations are interpreted as defects and, hence, are ignored for the collection of the subtrahend spectra.

For a quantification of the similarity the quadratic distance of the currently collected deviation from the current subtrahend spectrum is determined and used.

$$Dev = (\Delta r_1)^2 + (\Delta r_2)^2 + (\Delta r_3)^2 + \ldots (\Delta r_w)^2$$

with:
$\Delta r$=difference spectrum (see item 3)
W=number of the measured spectral points case: $Dev < \varepsilon$ $$r = \frac{1}{1+G}(r + Gx)$$

If the deviation (Dev) is smaller than an adjustable threshold ($\varepsilon$), the currently viewed spectrum x will be similar to the current subtrahend spectrum. In this case, the minuend spectrum (x) will be integrated in the current subtrahend spectrum. There is realised an adjustment of the reference spectrum to the changing conditions. If the deviation differs too much from the original reference spectrum ("first formula"), this will be notified of, thus requiring approval by the user.

Figure 8:
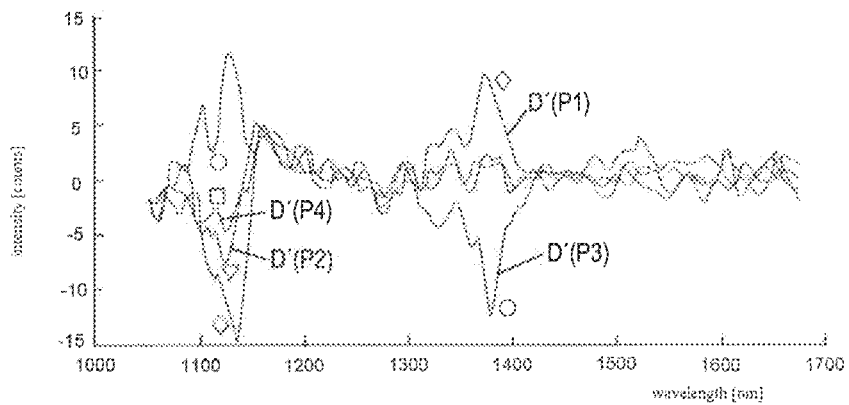
FIG. 8 shows a diagram of the first derivative of the difference curves of spectral light measurement signals shown in FIG. 7.

In order to obtain completely different but also significant signal curves, the nth derivative is to be calculated from the difference curves D(P1), D(P2), D(P3), D(P4) of the diagram of FIG. 7. The advantage of this embodiment is that the calculations are independent of the intensity and thus of changing illumination situations, as only the changes are included in the evaluation. The diagram of FIG. 8 shows the signal curves D'(P1), D'(P2), D'(P3), D'(P4) of the first derivative of the difference curves D(P1), D(P2), D(P3), D(P4), which constitute a classification feature. As sugar end criteria herein there may be determined, for example, an averaged negative differential quotient value, in the wavelength range between 1100 and 1200 nm, and an averaged positive differential quotient value in the wavelength range between 1300 and 1400 nm. These criteria are fulfilled by the signal curve D'(P1) of the locus point P1 and indicate a "sugar end" defect. In general, a classification feature may be the presence of differential quotient values within or out of a defined differential quotient value range at defined wavelengths or wavelength bands, optionally calculating the average value of the differential quotient values within the wavelength bands, and/or the similarity of at least one portion of the differential quotient curve with a predefined pattern.

Figure 11:
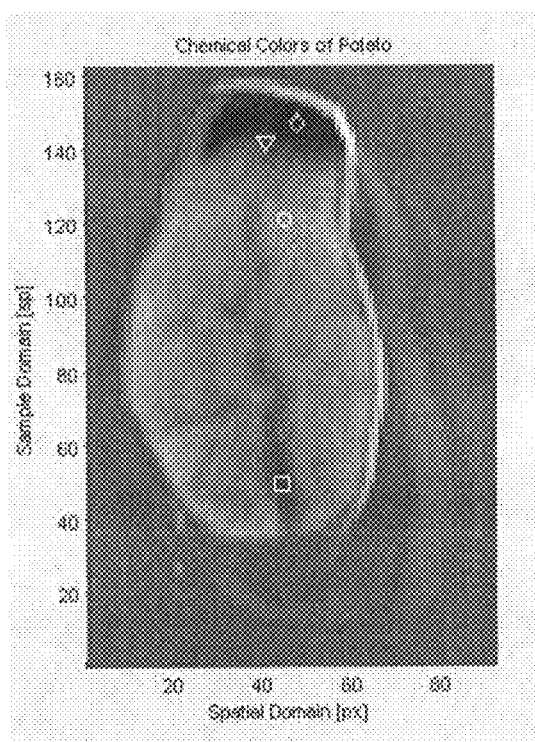
FIG. 11 shows an illustration of the potato of FIG. 5, which has been calculated according to the inventive method as a false-colour image on the basis of spectral difference curves.

In another embodiment of the inventive method, there is obtained a classification feature derived from the difference curves from the at least portion-wise transformation of the difference curves D(P1), D(P2), D(P3), D(P4) of the diagram of FIG. 7, or from the diagrams of FIG. 6 and especially FIG. 8 into a visible wavelength range, thereby giving "false-colour images". Preferably, there are transformed at least three portions of the difference curves into visible wavelength ranges, and the classification criterion is the locally defined appearance and/or absence of colours or colour ranges or colour transitions in the false-colour images. In this connection, there need not be used specific colours, but there may be rather used colour ranges (colour clouds), similar colours, etc. The advantage of the colour transformation: it compensates heterogeneities of the material. FIG. 11 shows an image of the potato K of FIG. 5, which has been calculated according to the inventive method as a false-colour image on the basis of difference curves. The sugar end region Z on the upper end of the potato K is clearly visible.

The transformation into the visible (VIS) wavelength range allows for the depiction of a spectrum by the three basic colours (RGB). If the spectral information changes, also the colour will change. If the spectral information is similar, also the colour representation will be similar.

In the case of sugar end detection, three features are calculated from the prepared spectrum, which are associated with the colour channels red (R), green (G) and blue (B) according to scaling.

Determination of the Colour Features

For the determination of the colour features, there is available a number of possibilities. For the sugar end detection, the calculation type "spectral range intensity" has proven to be suitable.

Spectral Range Intensity

The feature spectral range intensity multiplies the spectrum to be transformed with a filter curve. The result is a scalar (one-dimensional value).

$$F = \frac{1}{W}\sum_{i=1}^{W} y_i h_i$$

with:
F=value for the feature,
y=prepared spectrum,
h=filter curve,
i=wavelength index
W=number of the wavelength points of the spectrum y.

For a better understanding, this process may be explained by way of a standard colour camera system. By optical filters applied to the sensor the incident spectral information of the light is transformed into an intensity value conditioned by the filter characteristic. If there is used a green filter, for example, the spectral information in the range of blue and red will be subdued, whereas the light intensity in the spectral range of green may pass through. The irradiated sensor pixel, hence, provides a value corresponding to the average optical incidence in the spectral range of green. The result of the feature spectral range intensity may be compared with this value.

The filter curves are dependent on the application and are pre-determined by the application engineer. This may be carried out manually, but also using an automated calculation of suitable filter curves (optimization method).

Multi-Variant Collection of Spectral Differences

This method does not differ from the feature type "spectral range intensity" in regard to the (inline) calculation of the feature values. Also herein, a feature value is calculated by multiplication of a transformation vector (filter curve) with the spectrum. The difference is exclusively that the elaboration of ideal "filter curves" is carried out in automated way during offline calibration.

For calibration, there are selected spectrum sets, which represent materials to be distinguished. In the course of calibration, differences between the spectra are identified by using multi-variant data analysis methods. Finally, the user defines which differences are to be presented as a colour.

Mapping of the Feature Values to the Colour Space

As a rule, every feature type presents values in any range. If, for example, an intensity spectrum is multiplied with a filter curve, the value range of the features will be dependent on the value range of the spectrum and the filter curve. Significant changes in the spectrum will disperse the values over a wide range. It is easily understandable that the feature values may also have negative values. For colour representation, however, the value range is clearly defined, conditioned by a defined image format (e.g., 3×8 bit for R, G and B—in this case each of the colour values has to lie within the range 0 . . . 255). For this reason, a mapping of the feature values to be expected onto a defined value range is necessary.

Colour Manipulation Methods—Adjustment of Chemical Colour Images (CCI) Towards the Requirements of the Target Application The adjustment of a CCI (chemical colour image) may cause a valuable increase of the suitability of the image for a target application. In image processing, there is available a number of methods, which are used for adjusting colour information. The following methods are well-known and widely established: contrast, saturation, brightness and gamma manipulation.

The first step of colour manipulation enables the generation of non-linear relations between the feature values and the colour in the original image (e.g., for gamma correction). In this way, e.g., marking of differences at low intensities is possible. In order to provide for as much scope as possible, this relation is individually performed using a look up table (LUT) for every colour feature.

$$F_{sLUT} = LUT(F_s)$$

Operations on the basis of contrast and saturation may be carried out by means of a colour transformation. Therefore, a colour triple is multiplied with a 3×3 colour transformation matrix.

$$[F'_{sRED} F'_{sGREEN} F'_{sBLUE}] = [F_{sLUTred} F_{sLUTgreen} F_{sLUTblue}] \begin{bmatrix} c11 & c12 & c13 \\ \cdots & \cdots & \cdots \\ c31 & c32 & c33 \end{bmatrix}$$

The colour transformation matrix C is elaborated in the course of calibration. Adjustment of this matrix in inline operation may be advantageous for a "faster" adjustment of the chemical colours to the target application.

Classification of Sugar End Defects in Chemical Colour Images

Figure 9:
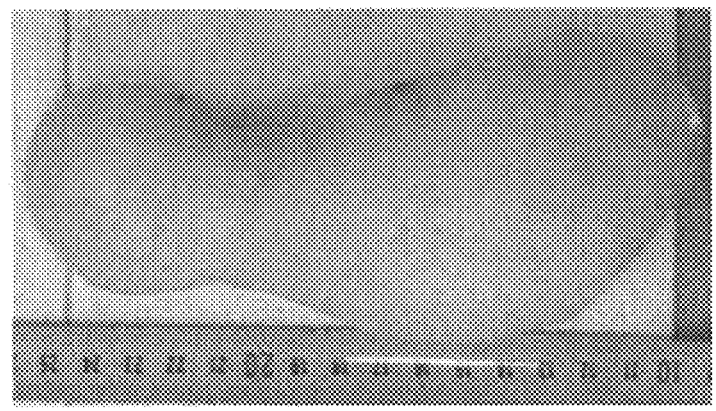
FIG. 9 shows an illustration of a (peeled) potatoe captured by a digital camera.
Figure 10:
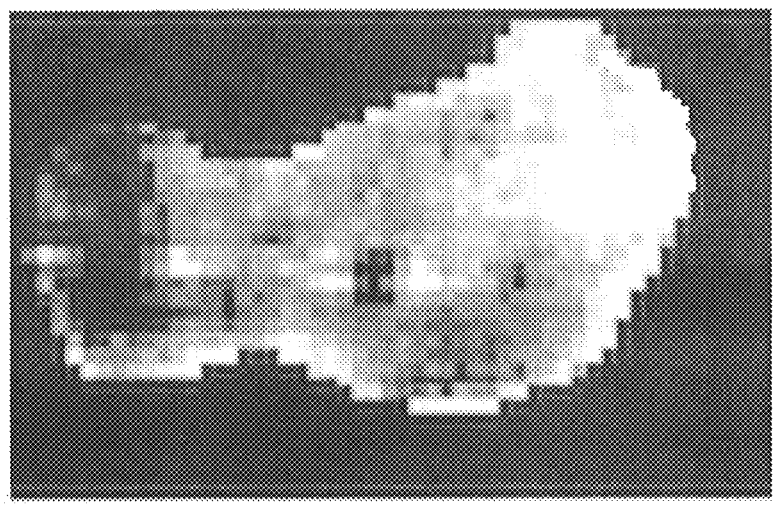
FIG. 10 shows an illustration of the potato of FIG. 9, which has been calculated according to an embodiment of the inventive method (ingredient glucose).

This is realized on the basis of implemented methods pertaining to the field of industrial colour processing. In the suitable interpretation of the filter curves or the application of multi-variant data processing, respectively, the sugar ends appear in a clearly different colour, as a result of the significantly different sugar content at this point. FIG. 9 shows an image of a potato captured by a digital camera. FIG. 10 shows an image of the potato of FIG. 9, which has been calculated according to the above method, in the special embodiment as a black-and-white image. The bright right region in the calculated image of FIG. 10 coincides with high glucose content and thus indicates a sugar end, whereas the remaining potato has darker regions indicating a low sugar content. In the digitally captured image of FIG. 9, however, there is only recognizable a slight glassiness in the right-hand end region, if at all, but this feature is too less pronounced in order to be interpreted as a "sugar end" defect.

In principle, the chemical colour imaging method is excellently suited to determine at least one classification feature from the respective spectrum or the nth derivative of the respective spectrum of the locus points, by identifying concentrations of ingredients such as, e.g., glucose, starch, solids, and/or by determining the glassiness from the spectrum or the nth derivative of the spectrum of the respective locus point. Classification features may be selected from the identified concentration values of the ingredients or combinations thereof, such as, e.g., the ratio of glucose to starch, and/or the glassiness.

The invention claimed is:

1. A method for detecting "sugar end" defects in potatoes, comprising: irradiating potatoes with at least one light source with wide-band light, for a plurality of locus points on each potato, wherein locus points lie on both end regions of the potato and other locus points lie in a central region of the potato, selectively projecting the light reflected from or transmitted through the respective locus points onto at least one photo sensor, generating, with the at least one photo sensor, light measurement signals for each locus point from the received light which light measurement signals are generated as the spectra of the light reflected from or transmitted through the locus points, and intermediately storing such light measurement signals generated for each locus point, determining at least one classification feature from the light measurement signals in a wavelength range between 350 and 2500 nm by determining at least one classification feature from the spectra of the nth (n=1, 2, . . . ) derivative of the spectra, and classifying potatoes as having "sugar end" defects if at least one classification feature corresponds to a predefined "sugar end" criterion, wherein determining at least one classification feature from the respective spectrum or the nth derivative of the respective spectrum of the locus points comprises calculating the difference curve for the respective locus point by calculating the differences between the spectral light measurement signals of the respective locus point and the spectral values of a reference spectrum for a number of wavelengths or by calculating the differences between the nth derivative of the spectral light measurement signals of the respective locus point and the nth derivative of the reference spectrum for a number of wavelengths, and that the classification feature is thus determined by the difference curve calculated in this way, wherein a classification feature derived from the difference curves is the curve of the first or second differential quotient of the respective difference curve and the classification criterion is selected from exceeding or falling below limit values of the differential quotient at defined wavelengths or wavelength bands, optionally with calculating average values of the differential quotient values within the wavelength bands, or the presence of difference quotient values within or out of a defined differential quotient value range at defined wavelengths or wavelength bands, optionally with calculating average values of the differential quotient values within the wavelength bands, or the similarity of at least one portion of the differential quotient curve with a predefined pattern.

2. A method according to claim 1, characterized in that the light reflected from or transmitted through the locus points is sequentially projected onto the at least one photo sensor.

3. A method according to claim 2, characterized in that the potatoes are moved along a conveying direction at a defined conveying velocity and that the light reflected from or transmitted through the locus points is projected successively onto the same photo sensor, spaced apart in time.

4. A method according to claim 3, characterized in that a plurality of photo sensor is arranged distributed transversely to the conveying direction, wherein—viewed in the conveying direction—locus points that are situated one after the other are each associated with the same photo sensor.

5. A method according to claim 1, characterized in that the light measurement signals contain light intensity values for a wavelength or wavelength band or contain several wavelengths or wavelength bands spaced apart, wherein the classification feature is these light intensity values and wherein the "sugar end" criterion is defined as the deviation from a threshold light intensity value.

6. A method according to claim 5, characterized in that the light intensity values are obtained at the particular wavelengths or wavelength bands by way of parallel or sequential irradiation of the potatoes with narrow-band light having the particular wavelengths or wavelength bands or by way of irradiation of the potatoes with wide-band light and filtering of the light reflected or transmitted at the respective locus points with band pass filters, the pass bands of which containing the particular wavelengths or wavelength bands or by way of provision of photo sensors, which are sensitive in the particular wavelengths or wavelength bands.

7. A method according to claim 1, characterized in that the respective light reflected from or transmitted through the locus points is received by splitting up the spectrum into a plurality of spectral components and that each spectral component is then projected onto one of the light-sensitive pixels associated with this spectral component of a photo sensor having a plurality of pixels, wherein the pixels of the photo sensor are optionally arranged in a two-dimensional way, wherein the first dimension represents the locus points and the second dimension represents the spectral components of the light.

8. A method according to claim 1, characterized in that a classification feature derived from the difference curves is the intensity curve of the respective difference curve over the wavelength and the classification criterion is selected from exceeding or falling below the intensity limit values at defined wavelengths or wavelength bands, optionally with calculating average values of the intensity values within the wavelength bands, or the presence of intensity values within or out of a defined intensity value range at defined wavelengths or wavelength bands, optionally with calculating average values of the intensity values within the wavelength bands, or the similarity of at least one portion of the intensity curve with a predefined pattern.

9. A method according to claim 1, characterized in that the reference spectrum is calculated as an averaged spectrum from the spectral image data of locus points of at least one potato, preferably from the spectral image data of locus points, which are associated with a centre region of one or several potatoes.

10. A method according to claim 9, characterized in that the reference spectrum is calculated or updated as a locally or timely averaged spectrum from the spectral image data of locus points of one or several potatoes to be examined in regard to "sugar end" defects, optionally while the potatoes are moved along the conveying direction.

11. A method according to claim 1, characterized in that determining at least one classification feature from the respective spectrum or nth derivative of the respective spectrum of the locus points comprises calculating the concentrations of ingredients, or evaluating the glassiness from the spectrum or from the nth derivative of the spectrum of the respective locus point, and that the classification features are selected from the determined concentration values of the ingredients or combinations thereof.

12. A method according to claim 11, characterized in that from the spectrum or the nth derivative of the spectrum of at least one locus point, wherein the locus point lies preferably in a central region of a potato, wherein optionally a plurality of locus points are used calculating the average value of their spectra or the nth derivative of the spectra, there are determined reference concentrations of ingredients or the glassiness, and that the deviation of the determined reference concentration values of the ingredients or combinations thereof or of the reference glassiness, from concentrations of ingredients or combinations thereof or from the glassiness at locus points, which lie on the end regions of potatoes, represent a "sugar end" criterion.

13. A method for detecting "sugar end" defects in potatoes, comprising: irradiating potatoes with at least one light source with wide-band light, for a plurality of locus points on each potato, wherein locus points lie on both end regions of the potato and other locus points lie in a central region of the potato, selectively projecting the light reflected from or transmitted through the respective locus points onto at least one photo sensor, generating, with the at least one photo sensor, light measurement signals for each locus point from the received light which light measurement signals are generated as the spectra of the light reflected from or transmitted through the locus points, and intermediately storing such light measurement signals generated for each locus point, determining at least one classification feature from the light measurement signals in a wavelength range between 350 and 2500 nm by determining at least one classification feature from the spectra or the nth derivative of the spectra, and classifying potatoes as having "sugar end" defects if at least one classification feature corresponds to a predefined "sugar end" criterion, wherein determining at least one classification feature from the respective spectrum or the nth derivative of the respective spectrum of the locus points comprises calculating the difference curve for the respective locus point by calculating the differences between the spectral light measurement signals of the respective locus point and the spectral values of a reference spectrum for a number of wavelengths or by calculating the differences between the nth derivative of the spectral light measurement signals of the respective locus point and the nth derivative of the reference spectrum for a number of wavelengths, and that the classification feature is thus determined by the difference curve calculated in this way, wherein a classification feature derived from the difference curves is obtained from the at least portion-wise transformation of the difference curves into a visible wavelength range, thereby obtaining false-colour images, wherein preferably at least three portions of the difference curves are transformed into visible wavelength ranges, and the classification criterion is the locally defined appearance or absence of colours or colour ranges or colour transitions in the false-colour images.

* * * * *